US012569269B2

(12) United States Patent
Wei et al.

(10) Patent No.:  US 12,569,269 B2
(45) Date of Patent:      Mar. 10, 2026

(54) BENDABLE CUTTING APPARATUS FOR MYOCARDIUM AND SYSTEM WITH THE SAME

(71) Applicant: Wuhan Wei NewTech Medical Co. , Ltd., Wuhan (CN)

(72) Inventors: Xiang Wei, Wuhan (CN); Jing Fang, Wuhan (CN); Rui Wang, Wuhan (CN); Rui Li, Wuhan (CN); Shuai Xu, Wuhan (CN); Fei Li, Wuhan (CN); Huixin Dai, Wuhan (CN); Yun Sun, Wuhan (CN)

(73) Assignee: Wuhan WeiNewTech Medical Co. , Ltd., Wuhan (CN)

( * ) Notice: Subject to any disclaimer, the term of this patent is extended or adjusted under 35 U.S.C. 154(b) by 381 days.

(21) Appl. No.: 18/192,821

(22) Filed: Mar. 30, 2023

(65) Prior Publication Data

US 2024/0023982 A1     Jan. 25, 2024

(30) Foreign Application Priority Data

Jul. 19, 2022    (CN) .......................... 202221888617.8

(51) Int. Cl.
| | |
|---|---|
| A61B 10/02 | (2006.01) |
| A61B 17/32 | (2006.01) |
| A61B 17/00 | (2006.01) |

(52) U.S. Cl.
CPC ................. A61B 17/320016 (2013.01); *A61B 2017/00243* (2013.01); *A61B 2017/00305* (2013.01); *A61B 2217/005* (2013.01)

(58) Field of Classification Search
None
See application file for complete search history.

(56) References Cited

U.S. PATENT DOCUMENTS

| | | | | | |
|---|---|---|---|---|---|
| 5,873,886 | A | * | 2/1999 | Larsen ............. | A61B 17/32002 606/167 |
| 5,976,164 | A | * | 11/1999 | Bencini .............. | A61B 10/0275 606/159 |
| 2005/0215922 | A1 | * | 9/2005 | Tsonton ............. | A61B 10/0275 600/566 |
| 2018/0333165 | A1 | * | 11/2018 | Algawi ............ | A61B 17/32002 |

FOREIGN PATENT DOCUMENTS

| | | |
|---|---|---|
| CN | 108478258 A | 9/2018 |
| CN | 112294399 A | 2/2021 |
| CN | 114419032 A | 4/2022 |

* cited by examiner

*Primary Examiner* — Etsub D Berhanu
(74) *Attorney, Agent, or Firm* — Nitin Kaushik

(57) ABSTRACT
A bendable cutting apparatus for myocardium and a system with the same are provided. The cutting apparatus includes a cutting portion, a bendable portion, and a driving portion. The bendable portion is connected between the cutting portion and the bendable portion, the cutting portion is driven by the driving portion to cut down a target, and the bendable portion is configured to bend in response to being tensioned and loosen by the driving portion.

14 Claims, 4 Drawing Sheets

BENDABLE CUTTING APPARATUS FOR MYOCARDIUM AND SYSTEM WITH THE SAME

CROSS-REFERENCE TO RELATED APPLICATIONS

The application claims priority to Chinese patent application No. CN202221888617.8, filed on Jul. 19, 2022, the entire contents of which are incorporated herein by reference.

TECHNICAL FIELD

The present application relates to a field of medical apparatus and instruments, and more particularly, to a bendable cutting apparatus for myocardium and a system with the same.

BACKGROUND

Hypertrophic obstructive cardiomyopathy is a myocardium morphological abnormal disease, the cause of which may be related to gene mutation, abnormal myocardial calcium dynamics and increased secretion of catecholamine. The pathology manifestation of the disease is asymmetric septal hypertrophy, hypertrophic myocardium projects into the left ventricle, which decreases the volume of the left ventricle, significantly increases the pressure step difference of the left ventricular outflow, results in systolic anterior motion and further exacerbates the obstruction of the left ventricular outflow. In turns, it results in obstruction of left ventricular bleeding and progressive deterioration of cardiac function. The disease clinical signs and symptoms mainly manifested as symptoms of heart failure such as chest pain, difficulty in breathing and syncope, untreated years fatality rate 1.7%~4%, mostly sudden death due to malignant arrhythmia, poor natural prognosis.

At present, the treatment methods of hypertrophic obstructive cardiomyopathy mainly include drug therapy, double-cavity pacing therapy, coronary septal alcohol ablation and open septal myocardium resection (Morrow surgical method and improved Morrow surgical method). Drug and double-cavity pacing therapy can only reduce myocardial oxygen consumption and alleviate heart failure symptoms to a certain extent, enhance patients' exercise tolerance, and cannot fundamentally remove the etiology, so the treatment effect is limited. Alcohol ablation results in partial myocardial infarction by injecting anhydrous alcohol into the first septal branch of the anterior left descending branch of the coronary artery, thinning the basal section of the hypertrophic septum, reducing hypertrophic obstruction and reducing the pressure step. However, this method still has great limitations: (1) it may cause non-target myocardial infarction to e abnormal myocardial motion and aggravate the condition. (2) it may cause high incidence of complications (about 10%) such as atrioventricular block and ventricular arrhythmia due to myocardial scarring. (3) about 5%~8% of patients are not subjected to alcohol ablation due to the variation of the first septal branch. (4) the short-term and long-term curative effects are inferior to open septal myocardium resection. (5) the malformation of mitral papillary muscle and abnormal valve structure could not be treated. In addition, although the septal radiofrequency ablation via percutaneous catheters has been attempted, it has not yet been widely used due to these complications.

Therefore, septal myocardium resection is still the best treatment for hypertrophic obstructive cardiomyopathy.

However, traditional septal myocardium resection still has many challenges and problems: (1) Since the heart is removed in the stopped state, the thickness and texture of the heart are different from the heart in the beat state, and the scope of removal is difficult to evaluate preoperative. It is completely dependent on the experience of the operator. Therefore, only a few experienced centers can complete the operation well, which is difficult to promote. (2) It is impossible to evaluate the removal effect in real time after removing. If the scope of removal is too wide, it may lead to perforation of ventricular septum and injury of conduction beam. (3) The surgical trauma caused by cardiac surgery and extracorporeal circulation leads to myocardial injury and systemic inflammatory. Therefore, the surgical method of septal myocardium resection still needs improvement.

SUMMARY

To solve at least one of the above technical solutions, the present application provides a bendable cutting apparatus for myocardium. The cutting apparatus comprises a cutting portion, a bendable portion, and a driving portion, the bendable portion is connected between the cutting portion and the bendable portion; wherein the cutting portion is driven by the driving portion to cut down a target, and the bendable portion is configured to bend in response to being tensioned and loosen by the driving portion.

In some embodiments of the present application, the bendable portion comprises a joint member having a plurality of joints, each of the plurality of joints is in a loose fit with an adjoining one of the plurality of joints, a front one of the plurality of joints is connected to the cutting portion, and a rear one of the plurality of joints is connected to the driving portion; wherein the plurality of joints is further connected together by a first rope and a second rope, the driving portion is configured to tension and loose the first rope and the second rope to bend the joint member.

In some embodiments of the present application, t in a case that the joint member is bent from a horizontal position to an upward vertical position, a bending angle ranges from 0° to 90°, and in a case that the joint member is bent from a horizontal position to a downward vertical position, the bending angle ranges from 0° to −90°.

In some embodiments of the present application, the driving portion comprises a bending button, a first screw rod, a second screw rod, a first screw plate, and a second screw plate; wherein the first screw rod is connected with the bending button, the second screw rod is connected to the first screw rod, the second screw rod has a screw direction different with a screw direction of the first screw rod, and the bending button is configured to rotate the first screw rod and the second first screw rod; wherein the first screw plate is threadedly connected with the first screw rod and is connected to the first rope, and the second screw plate is threadedly connected with the second screw rod and is connected to the second rope, so that the first rope and the second rope are tensioned and loosen in response to rotation of the first screw rod and the second first screw rod.

In some embodiments of the present application, the cutting portion has a cutter configured to cut down the target, the cutter is connected to the driving portion by a first shaft, and the driving portion is further configured to drive the cutter to move linearly and rotate along a long axis of the cutting apparatus.

In some embodiments of the present application, the cutting portion further has a cavity, the cutter is provided in the cavity, and a groove is provided on a wall of the cutting portion to receive the target; wherein the cutter is further configured to extend through the groove and return back to the cavity in response to being moved linearly by the driving portion, and the cutter has an arc surface corresponding to an inner surface of the cavity.

In some embodiments of the present application, a plurality of holes is provided in the groove, and a suction tube is connected to the cavity to suck air in the cavity by a negative pressure, so that the target is firmly absorbed in the groove.

In some embodiments of the present application, the driving portion further comprises a cutting button connected with the first shaft, and the cutting button is configured to drive the cutter to move linearly and rotate along the long axis of the cutting apparatus.

In some embodiments of the present application, the cutting button is operated manually or driven by a motor.

In some embodiments of the present application, the cutting portion further comprises a puncture needle provided in the cavity, the puncture needle is connected to the driving portion by a second shaft and is driven by the driving portion to move along the long axis of the cutting apparatus.

In some embodiments of the present application, the second shaft is extended in the first shaft, a connecting block is provided at a front end of the second shaft, and the puncture needle is provided at a lower position on the connecting block to puncture through the groove.

In some embodiments of the present application, the puncture needle is provided inclined downward.

In some embodiments of the present application, the driving portion further comprises a slider connected with the second shaft, and the slider is configured to move the second shaft linearly in the first shaft, so that the puncture needle is extended through the groove to puncture the target.

In some embodiments of the present application, the slider is operated manually or driven by a motor.

The present application further provides a system with bendable cutting apparatus for myocardium, wherein the system includes the bendable cutting apparatus for myocardium of above, a sheath and a traction wire.

Compared with the prior art, the device has the functions of removing septal hypertrophy from multiple angles and modifying abnormal papillary muscles, and can be applicable to the part of hypertrophy that is difficult to remove due to the change of angle position during the removal of septal hypertrophy, as well as the cutting part of the root of abnormal papillary muscles, so that the left ventricular outflow channel is more completely cleared, the difficulty of surgery is reduced, and the surgical effect is optimized.

For the above scheme, the utility model describes the disclosed exemplary embodiments in detail by referring to the drawings below, and other features and advantages of the embodiments of the utility model are also clear.

BRIEF DESCRIPTION OF DRAWINGS

The above and/or additional aspects and advantages of the present application will become apparent and readily understood from the following description of embodiments taken in conjunction with the accompanying drawings.

DETAILED DESCRIPTION OF THE EMBODIMENTS

Figure 1:
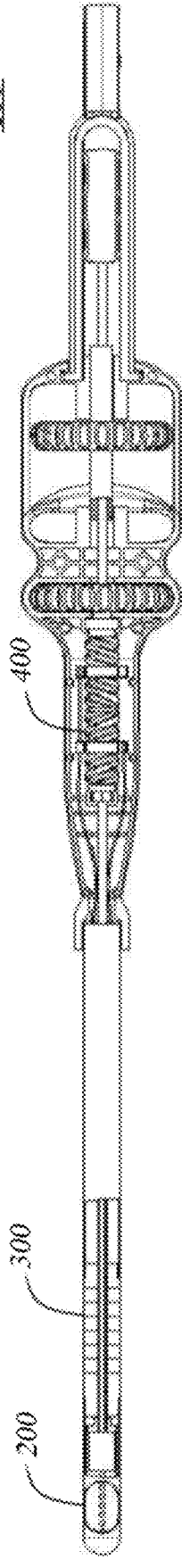
FIG. 1 is a schematic diagram of a bendable cutting apparatus for myocardium according to the present application.

In order to facilitate understanding of this application, this application is more fully described below with reference to the related drawings. The embodiments of the present application are shown in the drawings. However, this application can be implemented in many different forms and is not limited to the embodiments described herein. Conversely, the purpose of providing these embodiments is to make the disclosure of this application more thorough and comprehensive. The embodiments described below by reference to the accompanying drawings are exemplary and are merely illustrative of the present application and are not to be construed as limiting the application.

In the description of this application, it should be understood that the azimuth or positional relationship indicated by the terms "center", "central portion", "longitudinal", "transverse", "length", "width", "thickness", "upper", "lower", "front", "rear", "left", "right", "vertical", "horizontal", "top", "bottom", "inner", "outer", "axial", "radial", "circumferential", and the like, is based on the azimuth or positional relationship shown in the drawings, merely for ease of description of this application and simplification of the description, and is not intended to indicate or imply that the device or element referred to must have a particular azimuth, be constructed and operated in a particular azimuth, and therefore is not to be construed as limiting the application. Further, features defining by "first" and "second" may explicitly or implicitly include one or more these features. In the description of this application, unless otherwise stated, "plurality" means two or more.

In the description of the present application, it should be understood that, unless expressly stated and defined otherwise, the terms "mount", "conduct", "connect" are to be understood in a broad sense, for example, as a fixed connection, as a detachable connection, or as an integrated connection. It may be a mechanical connection or an electrical connection. It may be directly connected or indirectly connected by means of an intermediate medium, and it may be internal communication of the two elements. The specific meaning of the above terms in the present application can be understood in a specific way to those of ordinary skill in the art.

When used here, singular forms of "a", "one" and "the" can also include plural forms unless the context clearly indicates another way. It should also be understood that the terms "comprise/include" or "have" indicate the existence of the stated features, whole, steps, operations, components, parts, or combinations thereof, but not rule out the possibility of the existence or addition of one or more other features, whole, steps, operations, components, parts, or combinations thereof.

In addition, the expressions "proximal" and "distal" of the feature in the embodiment are relative expressions of the feature's proximity or distance to the human body or the operator. For example, the part of the instrument that interferes with the human body is regarded as distant from the operator. The part placed outside the body near the operator is considered to be proximal.

A bendable cutting apparatus for myocardium is provided according to the present application. As shown in FIG. 1, the bendable cutting apparatus 100 for myocardium may be a minimally invasive cardiac surgical instrument. The bendable cutting apparatus 100 for myocardium includes a cutting portion 200, a bendable portion 300, and a driving portion 400, wherein the bendable portion 300 is connected between the cutting portion 200 and the driving portion 400. The cutting portion 200 is driven by the driving portion 400 to cut down a target, wherein the target may be a target tissue, for example a hypertrophy tissues on the myocardium. The hypertrophy tissues is taken as the target for description below. The bendable portion 300 is configured to bend in response to being tensioned and loosen by the driving portion 400. Specifically, in use, the driving portion 400 is held and controlled by the operator. The cutting portion 200 is moved to the hypertrophy tissues by the operator via the driving portion 400, and then, the driving portion 400 is operated to tension and loose the bendable portion 300 to bend, as such, the cutting portion 200 is adjusted to a proper angle or position relative to the hypertrophy tissues. The operator can use the driving portion 400 to control and adjust the bending angle of the bendable portion 300 until a final angle or position of the cutting portion 200 relative to the hypertrophy tissues is obtained. Meanwhile, the operator controls the driving portion 400 to drive the cutting portion 200 to cut down the hypertrophy tissues.

By providing the bendable portion 300, the angle or position of the cutting portion 200 relative to the hypertrophy tissues is advanced adjusted, and the cutting apparatus 100 can be applied for cutting the hypertrophy tissues from multiple angles. As such, the cutting apparatus 100 has the functions of removing septal hypertrophy tissues from multiple angles and modifying abnormal papillary muscles, and can be applied to some hypertrophic tissues that are difficult to be removed due to changes in angle position during the removal of septal hypertrophy, as well as the cutting part of the root of abnormal papillary muscles, so that the left ventricular outflow channel is more completely cleared, the difficulty of surgery is reduced, and the surgical effect is optimized.

Figure 3:
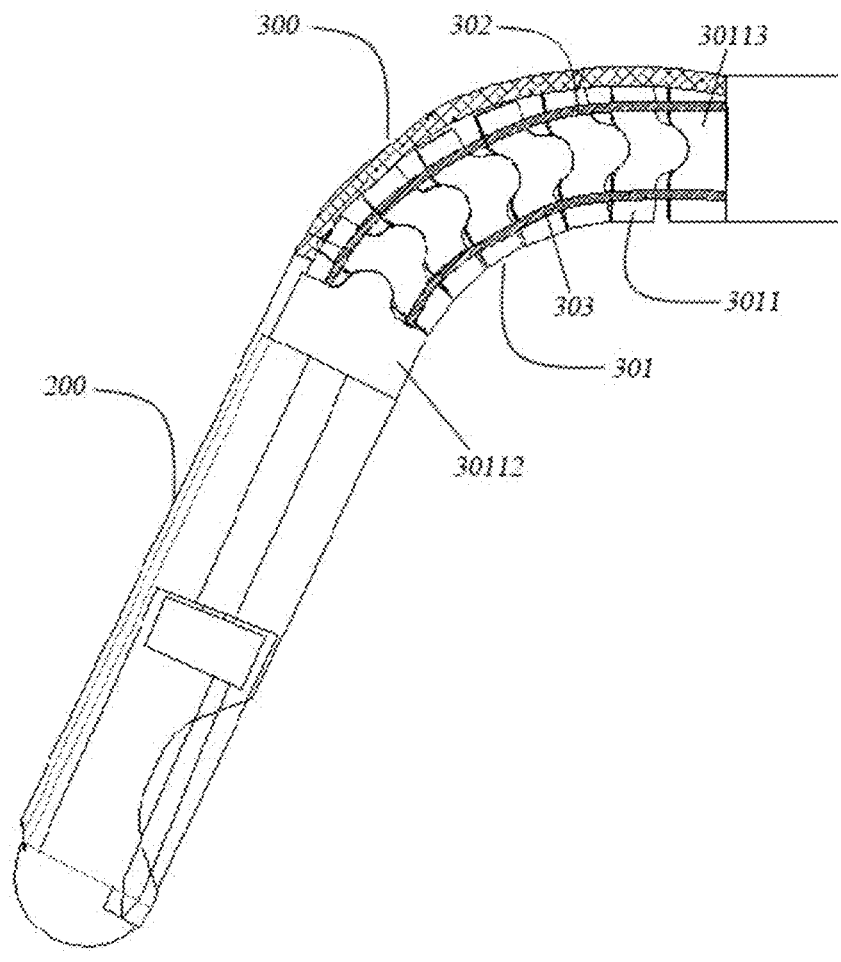
FIG. 3 is a schematic diagram of a cutting portion and a bendable portion of a bendable cutting apparatus for myocardium according to the present application.

In an embodiment, as shown in FIG. 3, the bendable portion 300 comprises a joint member 301, wherein the joint member 301 is disposed between the cutting portion 200 and the driving portion 400, and has a plurality of joints 3011. Exemplarily, a front one 30112 of the plurality of joints is connected to the cutting portion 200, and a rear one 30113 of the plurality of joints is connected to the driving portion 400.

Each of the plurality of joints 3011 is in a loose fit with an adjoining one. Further, the plurality of joints 3011 is further connected together by a first rope 302 and a second rope 303, and the first rope 302 and the second rope 303 are connected to the driving portion 400. As such, the driving portion 400 may apply a tension force and a loose force to the first rope 302 and the second rope 303, respectively, and the first rope 302 and the second rope 303 further to tension and loose the plurality of joints 3011. The plurality of joints 3011 may connect closely with each other when a tension force is applied, and the plurality of joints 3011 may connect loosely when a loose force is applied. Further, the joint member 301 is presented in bending as the plurality of joints 3011 connects closely and loosely with each other, and the details are described below.

Figure 6:
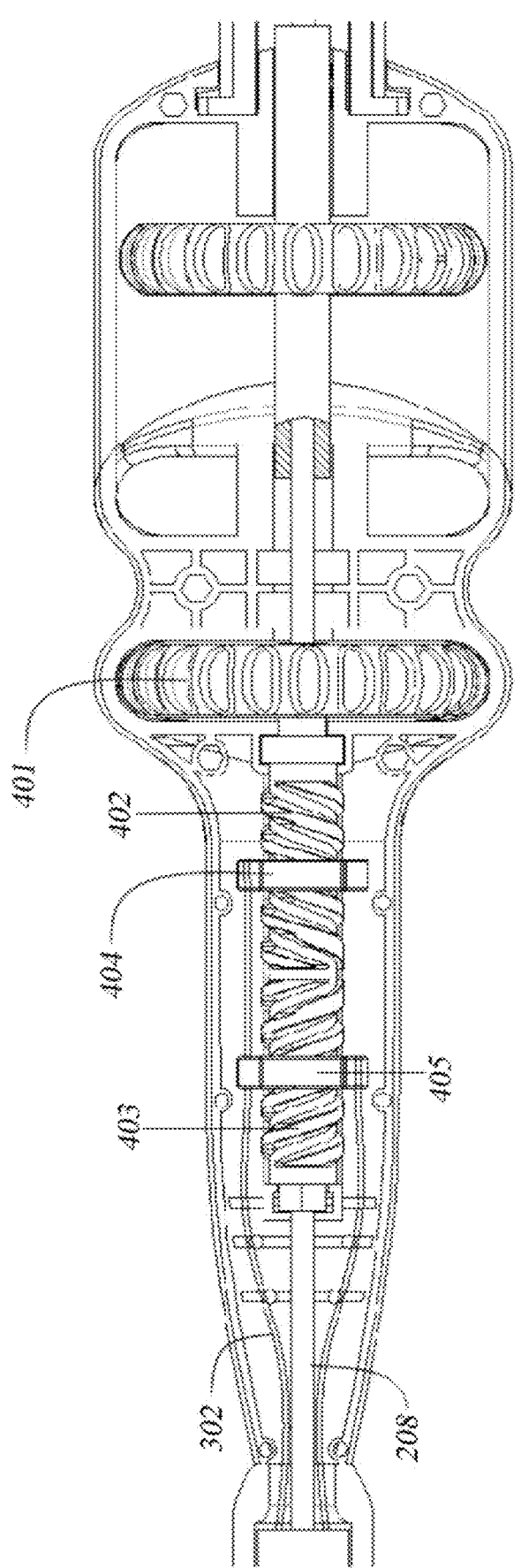
FIG. 6 is an enlarged schematic diagram of a bendable portion of a bendable cutting apparatus for myocardium according to the present application.

Combined with FIG. 6, the driving portion 400 comprises a bending button 401, a first screw rod 402, a second screw rod 403, a first screw plate 404, and a second screw plate 405. The first screw rod 402 is connected with the bending button 401, the second screw rod 403 is connected to the first screw rod 402, the second screw rod 403 has a screw direction different with a screw direction of the first screw rod 402. The first screw plate 404 is threadedly connected with the first screw rod 402 and is moveable along the first screw rod 402. The first screw plate 404 is further connected to the first rope 302. The second screw plate 405 is threadedly connected with the second screw rod 403 and is moveable along the second screw rod 403. The second screw plate 405 is further connected to the second rope 303. The bending button 401 is configured to rotate the first screw rod 402 and the second first screw rod 403. A first window (not shown) may be provided on the cutting apparatus 100 for operating the bending button 401.

When the first screw rod 402 is rotated clockwise, the first screw plate 404 moves forward along the first screw rod 402 to loosen the first rope 302. Since the second screw rod 403 has different screw direction with the first screw rod 402, the second screw plate 405 moves backward along the second screw rod 403 to tension the second rope 303. The parts of the plurality of the joints 3011 connected to the first rope 302 are connected loosely, and parts of the plurality of the joints 3011 connected to the second rope 303 are connected closely. At this time, the joint member 301 is bent downward. When the first screw rod 402 is rotated counterclockwise, the first screw plate 404 moves backward along the first screw rod 402 to tension the first rope 302 and the second screw plate 405 moves forward along the second screw rod 403 to loosen the second rope 303. The parts of the plurality of the joints 3011 connected to the first rope 302 are connected closely, and parts of the plurality of the joints 3011 connected to the second rope 303 are connected loosely. Thus, the joint member 301 is bent upward.

During the joint member 301 is bent from a horizontal position to an upward vertical position, the bending angle can be adjusted from 0° to 90°. During the joint member 302 is bent from a horizontal position to a downward vertical position, the bending angle can be adjusted from 0° to −90°. This is, the bending angle of the joint member ranges from −90° to 90°.

In an embodiment, a first rail and a second rail (not shown) are provided in the driving portion 404. The first rail is disposed corresponding to the first rope 302, and is slidably connected with corresponding sides of the first screw plate 404 and the second screw plate 405. The second rail is disposed corresponding to the second rope 303, and is slidably connected with another corresponding sides of the first screw plate 404 and the second screw plate 405.

Figure 2:
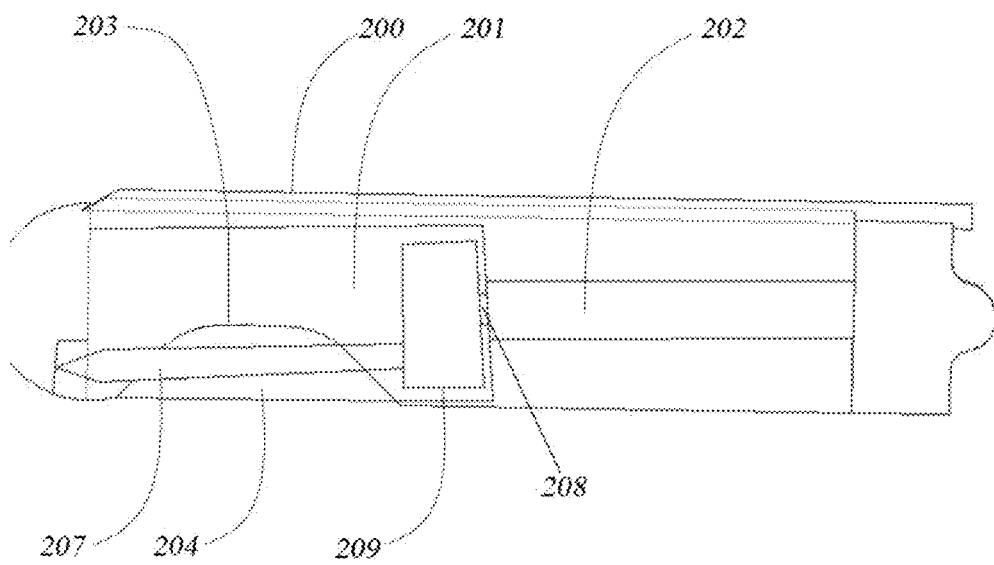
FIG. 2 is schematic diagram of a cutting portion of a bendable cutting apparatus for myocardium according to the present application.

Combined with FIG. 2, the cutting portion 200 has a cutter 201 configured to cut down the hypertrophy tissues, and the cutter 201 is connected to the driving portion 400 by a first shaft 202. The driving portion 400 is further configured to drive the cutter 201 to move linearly and rotate along a long axis of the cutting apparatus 100. The cutter 201 is moved linearly to close to or away from the hypertrophy tissues for a primary position, and then a secondary position is provided by the bendable portion 300. After an accurately position is ensured, the cutter 201 is rotated to cut down the hypertrophy tissues.

In an embodiment, a groove 203 is provided on a wall of the cutting portion 200, the groove 203 can receive the hypertrophy tissues while forcing on the cutting portion 200 and/or the hypertrophy tissues. The cutting portion 200 further has a cavity 204, the cutter 201 is provided in the cavity 204. The cutter 201 is driven by the driving portion 400 to extend through the groove 203 to the hypertrophy tissues, and then to rotate to cut down the hypertrophy tissues.

In an embodiment, before performing the operation, the cutter 201 is operated to move linearly to and close the groove 203, and the heparin saline is injected into the cavity 204 (the way of injection will be discussed below), so that the cavity 204 and the groove 203 are filled with heparin saline to realize liquid seal and vent the air. Then, the cutting portion 200 is operated to close to the hypertrophy tissues, and the cutter 201 is moved to return back to the cavity 204 by the driving portion 400 to expose the groove 203. The hypertrophy tissues are forced into the groove 203. The cutter 201 is driven by the driving portion 400 to extend through the groove 203 to the hypertrophy tissues, and then to rotate to cut down the hypertrophy tissues.

In an embodiment, the cutter 201 has an are surface corresponding to an inner surface of the cavity 204. As such, the cutter 201 functions more effectively on closing the groove 203 and cutting the hypertrophy tissues in the groove 203.

Figure 4:
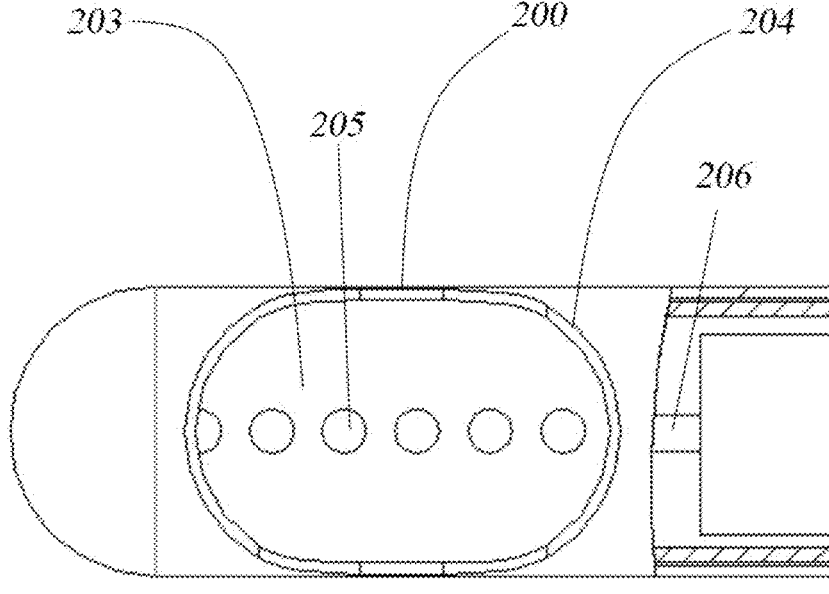
FIG. 4 is an enlarged schematic diagram of a cutting portion of a bendable cutting apparatus for myocardium according to the present application.

In an embodiment, as shown in FIG. 4, a plurality of holes 205 is provided in the groove 203, and a suction tube 206 (referring to FIG. 3) is connected to the cavity 204. The suction tube 206 is provided with a negative pressure source (not shown). The negative pressure source provides a negative pressure to suck the air in the cavity 204, and the air between the hypertrophy tissues and the groove 203, through the plurality of holes 205 and the suction tube 206. As such, the hypertrophy tissues can be firmly absorbed in the groove 203. In another embodiment, the heparin saline is injected into the cavity 204 by the suction tube 206.

Figure 5:
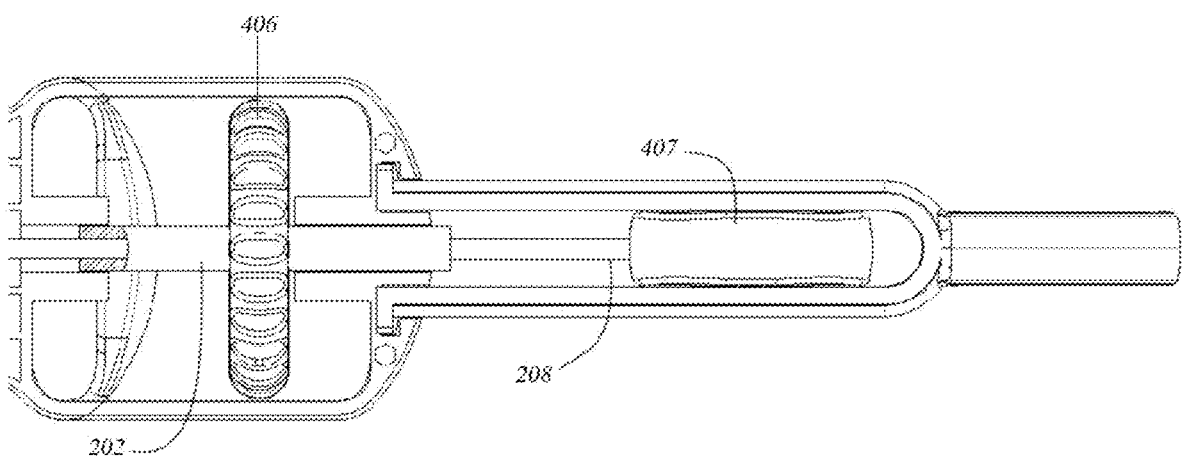
FIG. 5 is an enlarged schematic diagram of a driving portion of a bendable cutting apparatus for myocardium according to the present application.

In an embodiment, combined with FIG. 5, the driving portion 400 further comprises a cutting button 406 connected with the first shaft 202, and the cutting button 406 is configured to drive the cutter 201 to move linearly and rotate along the long axis of the cutting apparatus 100.

In an embodiment, the cutting button 406 is operated manually. Exemplarily, a second window (not shown) may be provided on the cutting apparatus 100 for operating the cutting button 406. The operator may slide the cutting button 406 from the second window to move the cutter 201 linearly, and may rotate the cutting button 406 from the second window to rotate the cutter 201. In another embodiment, the cutting button 406 may be driven by a motor to slide linearly and rotate along the long axis of the cutting apparatus.

In an embodiment, back to FIG. 2, the cutting portion 200 further comprises a puncture needle 207 provided in the cavity 204, the puncture needle 207 is connected to the driving portion 400 by a second shaft 208 and is driven by the driving portion 400 to move along the long axis of the cutting apparatus 100. Exemplarily, the puncture needle 207 is moved toward to the groove 203 and to puncture the hypertrophy tissues in the groove 203. As such, the hypertrophy tissues are firmly positioned in the groove 203 by puncturing, thereby facilitating for cutting the hypertrophy tissues. Moreover, the cut hypertrophy tissues are held in the groove 203 by the puncture needle 207 for an easy removal.

In an embodiment, the second shaft 208 is extended in the first shaft 202, a connecting block 209 is provided at a front end of the second shaft 208, and the puncture needle 207 is provided at a lower position on the connecting block 209. In an embodiment, the puncture needle 207 is provided inclined downward for puncturing the groove 203 easily and holding the hypertrophy tissues at a greater extent.

In an embodiment, back to FIG. 5, the driving portion 400 further comprises a slider 407 connected with the second shaft 208, and the slider 407 is configured to move the second shaft 208 linearly in the first shaft 202. A third window (not shown) may be provided on the cutting apparatus 100. The operator may slide the slider 407 from the third window, to extend the puncture needle 207 through the groove 203, to puncture the hypertrophy tissues.

A system with bendable cutting apparatus for myocardium is provided according to the present application. The system includes the bendable cutting apparatus 100 for myocardium of above, a sheath and a traction wire.

According to the present application, the cutting apparatus has the functions of removing septal hypertrophy tissues from multiple angles and modifying abnormal papillary muscles, and can be applied to some hypertrophic tissues that are difficult to be removed due to changes in angle position during the removal of septal hypertrophy, as well as the cutting part of the root of abnormal papillary muscles, so that the left ventricular outflow channel is more completely cleared, the difficulty of surgery is reduced, and the surgical effect is optimized.

The bendable cutting apparatus 100 for myocardium disclosed in the present application is applied to a new minimally invasive operation for the treatment of hypertrophic obstructive cardiomyopathy. The operation is described in combination with the cutting apparatus in the present application.

S100, before performing the operation, the operator pushes the cutting button 406 to move the cutter 201 along the long axis of the cutting apparatus 100 to close the groove 203; and then the operator injects the heparin saline into the suction tube 206 through the syringe, so that the cavity 204 and the groove 203 is filled with the heparin saline to realize liquid seal and vent the gas.

S200, the operator treats the gap between the fourth and fifth ribs of the patient's left front chest wall with an incision to enter the pericardium and expose the apex of the heart. A suture purse is formed at the apex, and an opening is formed by puncture at the central position of the suture purse. After performing the puncture, the operator uses a dilator to enlarge the opening of the apical puncture and fasten the dilator at the opening.

S300, the operator moves the cutting portion 200 and bendable portion 300 to the left ventricular chamber along the dilated opening at the apex, and localizes the target area, that is, the basal section of the septal hypertrophic that needs to be removed, under the guidance of esophagus ultrasound and three-dimensional esophagus ultrasound.

S400, the operator aligns the cutter 201 and the groove 203 to the target area, and then the operator rotates the bending button 401 to apply tension and loosen force on the first rope 302 and the second rope 303 to bend the joint member 301 of the bendable portion 300, to adjust the angle between the groove 203 (the cutter 201) and the target area.

S500, the operator pulls the cutting button 406 back to keep the cutter 201 away from the groove 203 so that the groove 203 is exposed/open completely. Then the operator forces on the cutting apparatus 100 to make the hypertrophy tissues into the groove 203. The operator starts the negative pressure source to suck the air in the cavity 204 and the air between the hypertrophy tissues and the groove 203 through suction tube 206 and the plurality of holes 205, thereby absorbing and holding the hypertrophic tissue in the target area in the groove 203.

S600, after the hypertrophic tissue is absorbed and held in the groove 203, the operator pulls the slider 407 to move the second shaft 208 linearly in the first shaft 202, so that the puncture needle 207 punctures the groove 203 and positions the hypertrophic tissue in the groove 203.

S700, the operator needs to judge whether chords and papillary muscle injury will occur or not by three-dimensional ultrasound when cutting hypertrophic tissue. If not, the operator pushes the cutting button 406 to move the cutter 201 to hypertrophic tissue, and then turns the cutting button 406 to rotate the cutter 201 to cut down the hypertrophic tissue in the groove 203.

S800, after cutting the hypertrophic tissue, the operator removes the cutting portion 200 and the bendable portion 300 from the opening along the dilator, removes the cut the hypertrophic tissues, and flushes the cutting apparatus 100 with heparin saline.

S900, the operator observes the effect of the removal of the hypertrophic tissues through the esophagus ultrasound.

If it is judged that the effect of cutting the hypertrophic tissues is not as expected, S100 to S800 are repeated until it is judged that the effect is as expected.

Preferably, doppler ultrasound is used to measure the pressure difference of the left ventricular outflow to value the effect of cutting the hypertrophic tissues.

Preferably, and when S400 is re-executed, the angle of the groove 203 relative to the hypertrophy tissues is continuously adjusted to adapt to the hypertrophy tissues of different parts. If necessary, the operator can connect the suction tube 206 to the pressure catheter, and measure the pressure difference of the left ventricular outflow in real time before the cutting portion 200 and the bendable portion 300 are removed, so as to observe the cutting effect in real time.

S1000, if the effect of cutting the hypertrophy tissues are as expected, the operator sutures the opening at the apex and closed the incision of the chest wall layer by layer.

A method of hypertrophic obstructive cardiomyopathy using the cutting apparatus according to the present application is provided. On one hand, it avoids the problem of excessive myocardial resection that may be caused by static cardiac resection, and avoids the risk of iatrogenic septal perforation. On the other hand, it avoids the problem that the scope of surgical resection is not good enough, and it reduces over-dependence on the experience of the surgeon. It significantly improves the surgical efficacy. The cutting apparatus integrates cutting and removal of hypertrophic tissues to prevent peripheral artery embolization caused by falling of hypertrophic tissue.

Further, the cutting apparatus is made of a good material of ultrasonic compatibility, which is convenient to guide the esophagus ultrasound. Through the small incision of the left front chest wall, the operation wound caused by opening the chest in the middle is avoided, and the patient recovers quickly. Cardiac beating operation avoids the application of cardiopulmonary bypass in conventional thoracic surgery, thus avoids myocardial ischemia reperfusion injury and cardiopulmonary bypass related complications. If there are unpredictable complications during the operation, it can be transferred to conventional thoracic surgery in time to avoid fatal complications caused by alcohol ablation and radiofrequency ablation.

In the description of this specification, reference to the terms "one embodiment," "some examples," "some embodiments," "illustrative embodiments," "examples," "specific examples," or "some examples," etc., means that a particular feature, structure, material, or characteristic described in connection with the embodiment or example is included in at least one embodiment or example of the present application. In the present specification, the schematic representation of the above references does not necessarily refer to the same embodiments or examples. Moreover, the specific features, structures, materials, or characteristics described may be combined in any one or more embodiments or examples in a suitable manner.

Although the embodiments of the present application have been described in detail with reference to the accompanying drawings, the present application is not limited to the above embodiments, and various changes may be made without departing from the spirit of the present application and the knowledge of ordinary skill in the art.

What is claimed is:

1. A bendable cutting apparatus for myocardium, comprising: a cutting portion, a bendable portion, and a driving portion, wherein the bendable portion is connected between the cutting portion and the driving portion; wherein the cutting portion is driven by the driving portion to cut down a target, and the bendable portion is configured to bend in response to being tensioned and loosened by the driving portion;

wherein the cutting portion has a cutter configured to cut down the target, the cutting portion further has a cavity, the cutter and a puncture needle are provided in the cavity, the cutter is connected to the driving portion by a first shaft, and the puncture needle is connected to the driving portion by a second shaft and is driven by the driving portion to move along a long axis of the cutting apparatus.

2. The bendable cutting apparatus for myocardium of claim 1, wherein the bendable portion comprises a joint member having a plurality of joints, each of the plurality of joints is fitted with an adjoining one of the plurality of joints, a front one of the plurality of joints is connected to the cutting portion, and a rear one of the plurality of joints is connected to the driving portion; wherein the plurality of joints is further connected together by a first rope and a second rope, and the driving portion is configured to tension and loosen the first rope and the second rope to bend the joint member.

3. The bendable cutting apparatus for myocardium of claim 2, wherein, in a case that the joint member is bent from a horizontal position to an upward vertical position, a bending angle ranges from 0° to 90°, and in a case that the joint member is bent from a horizontal position to a downward vertical position, the bending angle ranges from 0° to −90°.

4. The bendable cutting apparatus for myocardium of claim 1, wherein the driving portion comprises a bending button, a first screw rod, a second screw rod, a first screw plate, and a second screw plate; wherein the first screw rod is connected with the bending button, the second screw rod is connected to the first screw rod, the second screw rod has a screw direction different than a screw direction of the first screw rod, and the bending button is configured to rotate the first screw rod and the second first-screw rod; wherein the first screw plate is threadedly connected with the first screw rod and is movable along the first screw rod, and the first screw plate is further connected to the first rope; wherein the second screw plate is threadedly connected with the second screw rod and is movable along the second screw rod, and the second screw plate is further connected to the second rope; wherein the first rope and the second rope are tensioned and loosened in response to rotation of the first screw rod and the second screw rod.

5. The bendable cutting apparatus for myocardium of claim 1, wherein the driving portion is further configured to drive the cutter to move linearly and rotate along the long axis of the cutting apparatus.

6. The bendable cutting apparatus for myocardium of claim 5, wherein a groove is provided on a wall of the cutting portion to receive the target, the cutter is further configured to extend through the groove and return back to the cavity in response to being moved linearly by the driving portion, and the cutter has an arc surface corresponding to an inner surface of the cavity.

7. The bendable cutting apparatus for myocardium of claim 6, wherein a plurality of holes is provided on the groove, and a suction tube is connected to the cavity to suck air in the cavity by a negative pressure, so that the target is capable of being absorbed in the groove.

8. The bendable cutting apparatus for myocardium of claim 5, wherein the driving portion further comprises a cutting button connected with the first shaft, and the cutting button is configured to drive the cutter to move linearly and rotate along the long axis of the cutting apparatus.

9. The bendable cutting apparatus for myocardium of claim 8, wherein the cutting button is operated manually.

10. The bendable cutting apparatus for myocardium of claim 5, wherein the second shaft is extended in the first shaft, a connecting block is provided at a front end of the second shaft, and the puncture needle is provided at a lower end of the connecting block to puncture through the groove.

11. The bendable cutting apparatus for myocardium of claim 10, wherein the driving portion further comprises a slider connected with the second shaft, and the slider is configured to move the second shaft linearly in the first shaft, so that the puncture needle is extended out the first shaft and through the groove to puncture the target.

12. The bendable cutting apparatus for myocardium of claim 11, wherein the slider is operated manually.

13. The bendable cutting apparatus for myocardium of claim 1, wherein the puncture needle is provided inclined downward.

14. A system with bendable cutting apparatus for myocardium, characterized by comprising the bendable cutting apparatus for myocardium of claim 1, a sheath and a traction wire.

* * * * *